United States Patent

Araki et al.

[11] 4,069,385
[45] Jan. 17, 1978

[54] METHOD FOR THE PREPARATION OF OPTICALLY ACTIVE ALLYLIC ESTERS

[75] Inventors: Masashi Araki, Ibaraki; Tsuneyuki Nagase, Takatsuki, both of Japan

[73] Assignee: Sumitomo Chemical Company, Limited, Osaka, Japan

[21] Appl. No.: 692,510

[22] Filed: June 3, 1976

[30] Foreign Application Priority Data

June 3, 1975 Japan .................................. 50-67197
June 6, 1975 Japan .................................. 50-68843

[51] Int. Cl.$^2$ .................... C07C 69/145; C07C 69/24; C07C 69/78
[52] U.S. Cl. ............................ 560/106; 260/410.9 N; 260/463; 560/1; 560/84; 560/89; 560/90; 560/95; 560/111; 560/112; 560/113; 560/122; 560/123; 560/124; 560/193; 560/197; 560/198; 560/199; 560/201; 560/237; 560/238; 560/240; 560/241; 560/249; 560/254; 560/255; 560/262
[58] Field of Search ........ 260/476 R, 497 R, 410.9 N, 260/463, 475 N, 485 N, 468 H, 468 R

[56] References Cited

U.S. PATENT DOCUMENTS 3,956,404   5/1976   Walling ............................. 260/476 R

OTHER PUBLICATIONS

Kochi et al., J. Org. Chem., 30, 1862ff (1965).
Sosnovsky, Angew. Chem., Int. Ed. 3, 269–276 (1964).
Denny et al., J. Org. Chem., 30, 3151–3153 (1965).

*Primary Examiner*—Jane S. Myers
*Attorney, Agent, or Firm*—Birch, Stewart, Kolasch and Birch

[57] ABSTRACT

In the preparation of olefin derivatives having an ester group at the allylic position (hereinafter referred to as "allylic ester(s)") which comprises reacting an olefin having at least one hydrogen atom at the allylic position and which will produce an allylic ester having an asymmetric carbon atom with an organic peroxide in the presence of a copper catalyst, a method for producing optically active allylic esters characterized by using, as the copper catalyst, an optically active copper complex derived from an optically active compound selected from the group consisting of Schiff's bases of the formula:

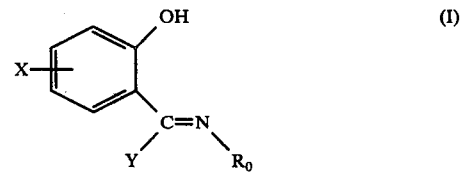

and amino acids of the formula:

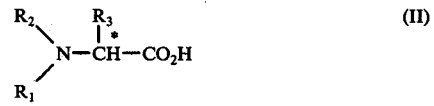

wherein $R_0$ is an optically active alkyl, cycloalkyl, aralkyl or aryl group which may contain an unsaturated bond and/or a substituent having a hetero atom, X and Y are each a hydrogen atom, an alkyl, cycloalkyl, aralkyl or aryl group, or a substituent having a hetero atom, $R_1$ and $R_2$ are each a hydrogen atom, or an alkyl, cycloalkyl, aralkyl or aryl group which may contain an unsaturated bond and/or a substituent having a hetero atom, $R_3$ is an alkyl, cycloalkyl, aralkyl or aryl group which may contain an unsaturated bond and/or a substituent having a hetero atom, or when $R_3$ is linked together with $R_2$, they form a divalent hydrocarbon group including or not including a hetero atom and which is optionally substituted with a substituent having a hetero atom, and the asterisk (*) indicates an asymmetric carbon atom.

9 Claims, No Drawings

METHOD FOR THE PREPARATION OF OPTICALLY ACTIVE ALLYLIC ESTERS

The present invention relates to a method for the preparation of optically active olefin derivatives having an ester group at the allylic position (hereinafter referred to as "allylic ester (s)"). More particularly, it relates to a method for the preparation of optically active allylic esters by asymmetric oxidation of olefins having at least one hydrogen atom at the allylic position.

In the present specification, the term "allylic ester" is intended to mean an ester derived from an olefin by substituting one hydrogen atom at the allylic position with an acyloxy group. The term "allylic position" means the position at the carbon atom adjacent to a double bond. For instance, the position at the carbon atom as underlined in the following formulae is the allylic position: $-CH_2-CH=CH_2$, $-CH(CH_3)-CH=CH_2$, $-CH=CH-CH_2-$, $-CH_2-CH=CH-CH_2-$, $-CH(CH_3)-CH=CH-CH_2-$, $-CH_2-C(CH_3)=CH_2$, $-CH_2-C(CH_3)=CH-CH_2$, etc.

Hitherto, there is known a method for the preparation of allylic esters by oxidation of an olefin with an organic peroxide using a copper salt as a catalyst, as disclosed in Jay K. Kochi and Harold E. Mains: J. Org. Chem., 30, 1862 (1965) and G. Sosnovsky: Angew. Chem., Int. Ed., 3, 269 (1964) as well as the literatures cited therein. However, optically active allylic esters can not be obtained by such method. On the other hand, there is reported a method for preparing optically active allylic esters in the system similar to that employed in the said method [cf. Donald B. Denny, Roger Napier and Arthur Cammarata: J. Org. Chem., 30, 3151 (1965)]. This method comprises oxidizing an olefin with a copper salt of an optically active carboxylic acid and t-butyl hydroperoxide to prepare the corresponding allylic ester of the carboxylic acid. In this method, however, the esters of optically active carboxylic acids obtainable are limited. Moreover, the use of a large amount of the optically active carboxylic acid is required since this reaction is not a catalytic reaction. Consequently, this method is not advantageous from the industrial point of view. Thus, no method for the preparation of optically active allylic esters by the catalytic asymmetric oxidation has been known.

It has now been found that optically active allylic esters are obtained using a certain optically active copper compound as the catalyst for the reaction as described above. The present invention is based on such finding.

According to the present invention, the optically active allylic esters can be prepared by reacting an olefin having at least one hydrogen atom at the allylic position with an organic peroxide in the presence of an optically active copper complex as a copper catalyst.

The optically active copper complex used as the copper catalyst in the present invention may be the one derived from a Schiff's base of the formula:

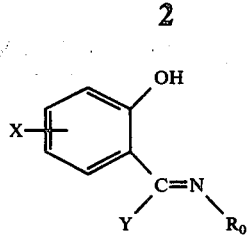

wherein $R_O$ is an optically active alkyl (preferably $C_4-C_{20}$ alkyl), cycloalkyl (preferably $C_4-C_{20}$ cycloalkyl) or aralkyl (preferably $C_8-C_{20}$ aralkyl) group which may contain an unsaturated bond and/or a substituent having a hetero atom, and X and Y are each a hydrogen atom, an alkyl (preferably $C_1-C_4$ alkyl) cycloalkyl (preferably $C_5-C_8$ cycloalkyl), aralkyl (preferably $C_7-C_{15}$ aralkyl) or aryl (preferably $C_6-C_{12}$ aryl) group, or a substituent having a hetero atom, or from an amino acid of the formula:

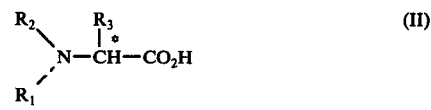

wherein $R_1$ and $R_2$ are each a hydrogen atom, or an alkyl (preferably $C_1-C_{10}$ alkyl), aralkyl (preferably $C_7-C_{15}$ aralkyl) or aryl (preferably $C_6-C_{15}$ aryl) group which may contain an unsaturated bond and/or a substituent having a hetero atom, $R_3$ is an alkyl (preferably $C_1-C_{10}$ alkyl), cycloalkyl (preferably cyclohexyl), aralkyl (preferably $C_7-C_{10}$ aralkyl) or aryl (preferably $C_6-C_{10}$ aryl) group which may contain an unsaturated bond and/or a substituent having a hetero atom, or when $R_3$ is linked together with $R_2$, they form a divalent hydrocarbon group including or not including a hetero atom (preferably $C_3-C_5$ alkylene) and optionally substituted with a substituent having a hetero atom, and the asterisk (*) indicates an asymmetric carbon atom.

In the above significances, the substituent having a hetero atom which may be present in the group represented by the symbol $R_0$ may be alkoxy (e.g. $C_1-C_{20}$ alkoxy), hydroxy, chlorine, bromine or the like. The substituent having a hetero atom represented by the symbol X or Y may be halogen (e.g. chlorine, bromine), alkoxy (e.g. $C_1-C_4$ alkoxy) or the like. As the substituent having a hetero atom which may be present in the group represented by the symbol $R_1$ to $R_2$, there are exemplified halogen (e.g. chlorine, bromine), alkoxy (e.g. $C_1-C_{10}$ alkoxy), cyano, amino, etc. As the substituent having a hetero atom which may be present in the group represented by the symbol $R_3$, there are exemplified alkoxy (e.g. $C_1-C_{10}$ alkoxy), hydroxy, methylsulfonyl, halogen (e.g. chlorine, bromine), etc. Examples of the divalent hydrocarbon group which may be formed by the symbols $R_2$ and $R_3$ when linked together are trimethylene, tetramethylene, etc., and examples of the substituent having a hetero atom with which the divalent hydrocarbon group may be substituted are halogen (e.g. chlorine, bromine), hydroxy, alkoxy (e.g. $C_1-C_{10}$ alkoxy), etc.

As the optically active copper complex derived from the Schiff's base (I), there are included various compounds. When, for instance, the Schiff's base is the one derived from salicylaldehyde, there are known the following four complexes [cf. R. H. Holm, G. W. Everett, Jr. and A. Chakravorty: Progress in Inorganic Chemistry, Vol. 7, John Wiley & Sons, Inc., New York, 1966, pp. 88 – 103]:

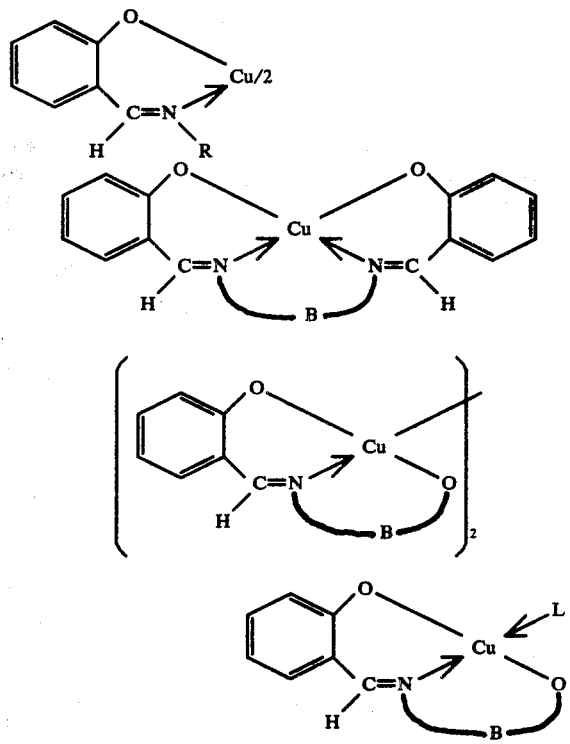

wherein B is an alkylene group and L is a neutral ligand like pyridine. All of them can be effectively used as the copper catalyst in the reaction of the present invention.

Those complexes may be prepared separately prior to the reaction of the present invention or formed in situ in the system of such reaction. Their preparation can be readily accomplished by treatment of a copper compound with the optically active Schiff's base (I) prepared from an optically active primary amine of the formula:

$$R_0-NH_2 \qquad (III)$$

wherein $R_0$ is as defined above and a salicylaldehyde compound of the formula:

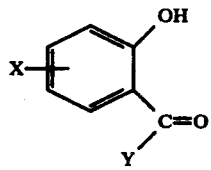

wherein X and Y are each as defined above according to a conventional procedure [cf. H. E. Smith, S. L. Cook and M. E. Warren, Jr.: J. Org. Chem., 29, 2265 (1964)].

Examples of the copper compound are cuprous or cupric carboxylates (e.g. formate, acetate, propionate, benzoate), halides (e.g. chloride, bromide, iodide), sulfate, nitrate, etc.

Examples of the optically active primary amine (III) are as follows:

a. 1-Phenylethylamine, 1-cyclopropylethylamine, 1-isobutylethylamine, 1-isopropylethylamine, 1-methylhexylamine, 1-phenyl-2-(p-tolyl)ethylamine, 1-(p-nitrophenyl)ethylamine, 1-(p-tolyl)ethylamine, 1-phenylpropylamine, 1-benzylethylamine, 1-thienylethylamine, 1-acetylbenzylamine, dehydroabiethylamine, alaninol, phenylalaninol, 1-methyl-1-phenylpropylamine, camphenylamine, menthylamine, 3-amino-3-deoxy-1,2-O-isopropylidene-5-O-triphenylmethyl-α-D-ribofuranose, etc.;

b. 2-Amino-1,1,3-triphenylpropanol-1,2-amino-1,1-di(o-anisyl)-3-phenylpropanol-1, 2-amino-1,1-di(2-methoxy-5-methylphenyl)-3-phenylpropanol-1, 2-amino-1,1-di(2-ethoxyphenyl)-3-phenylpropanol-1, 2-amino-1,1,4,4-tetra(o-anisyl)butane-1,4-diol, 2-amino-1,1-di(o-anisyl)-2-phenylethanol-1, etc.; and c. Amino acids such as alanine and phenylalanine.

Among these optically active primary amines as exemplified above, those which belong to Group (a) produce mononuclear copper complexes, and those which belong to Group (b) produce dinuclear copper complexes. The dinuclear copper complexes can be converted into the corresponding mononuclear ones. For example, treatment of the dinuclear copper complex with pyridine affords a mononuclear pyridinate complex.

Examples of the salicylaldehyde compound (IV) are salicylaldehyde, o-vanillin, 3,5-dibromosalicylaldehyde, 3-nitrosalicylaldehyde, 3-isopropyl-6-methylsalicylaldehyde, 2-hydroxyl-1-naphthaldehyde, 1-hydroxy-2-naphthaldehyde, o-hydroxyacetophenone, 2-hydroxybenzophenone, 2-hydroxy-4'-methoxybenzophenone, 2-acetyl-1-hydroxynaphthalene, ect.

As the optically active copper complex derived from the amino acid (II), there are known various cuprous or cupric complexes of amino acids, of which a typical one is the cupric complex of alanine represented by the formula:

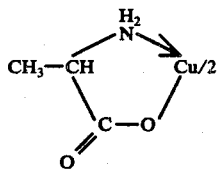

There are also known the complexes formed by coordinating neutral ligands such as water or ammonia to amino acidcopper complexes described above. These complexes may be prepared separately prior to the reaction of the present invention or formed in situ in the system of such reaction. Their preparation may be carried out by treatment by a copper compound with the amino acid (II) by a conventional procedure [cf. Gmelins Handbuch der Anorganischen Chemie (1966), "Copper" part B, section 4, pp. 1623 – 1650].

Examples of the copper compound are as mentioned above.

As the amino acid (II), there are exemplified the following compounds:

a. Amino acids (II) wherein $R_1$ and $R_2$ are each a hydrogen atom (e.g. alanine, valine, leucine, isoleucine, phenylglycine, phenylalanine, serine, threonine, ornithine, lysine, γ-oxylysine, glutamine, asparagine, cystine, methionine, tyrosine, proline, oxyproline, tryptophan);

b. Amino acids (II) wherein either $R_1$ or $R_2$ is a hydrogen atom (e.g. N-n-butylalanine, N-isobutylalanine, N-ethylvaline, N-n-propylvaline, N-n-butylvaline, N-isobutylvaline, N-n-heptylvaline, N-n-butylleucine, N-n-butylphenylglycine, N-(2-cyanoethyl)alanine, N-(2-cyanoethyl)valine, N-(2-cyanoethyl)leucine, N-(2-cyanoethyl)isoleucine, N-(2-cyanoethyl)phenylalanine, N-(2-cyanoethyl)tyrosine, N-(2-cyanoethyl)methionine, N-benzylalanine, N-benzylphenylalanine);

c. Amino acids (II) wherein neither $R_1$ nor $R_2$ is a hydrogen atom (e.g. N,N-dimethylalanine, N,N-dimethylvaline, N,N-dimethylleucine, N,N-dimethylphenylalanine, N,N-dimethyltyrosine, N,N-dimethylphenylglycine, N-methyl-N-ethylvaline, N-methyl-N-propylvaline, N-methyl-N-isobutylvaline, N-methyl-N-heptylvaline, N-(2-cyaloethyl)proline), etc.

The olefins used in the present invention are those which have at least one hydrogen atom at the allylic position. In view of the purpose of the present invention, however, the olefins which can not produce allylic esters having an asymmetric carbon atom such as propylene, 2-butene, 3-methyl-1-butene and 1,4-pentadiene are excluded. Specific examples of the usable olefins are cyclic olefins (e.g. cyclohexene, 1-methylcyclohexene, cyclopentene, 1,3-cyclohexadiene, cyclooctadiene, cyclododecatriene), non-cyclic olefins (e.g. 1-octene, 2-octene, 1-hexene, 2-hexene, 1-dodecene, 3-phenyl-1-propene, 1,3-diphenyl-1-propene, 1-naphthyl-1-propene, 4-phenyl-1-butene), etc. In general, preferred olefins may be chosen from $C_4-C_{12}$ acyclic olefins, $C_5-C_{12}$ cyclic olefins, $C_9-C_{24}$ aromatic group-substituted olefins, etc. These olefins may be optionally substituted with halogen (e.g. chlorine, bromine), alkyl such as one having not more than 4 carbon atoms, alkoxy such as one having not more than 4 carbon atoms, acyl such as alkanoyl having not more than 10 carbon atoms or alkoxycarbonyl having not more than 10 carbon atoms, acyloxy such as alkanoyloxy having not more than 10 carbon atoms, etc. The liquid olefins may serve as the reaction solvent by themselves.

As the organic peroxide, there are used hydroperoxides, diacyl peroxides, peroxy esters, dialkyl peroxides, etc. The hydroperoxides include those as representable by the formula:

$$R_4OOH \quad (V)$$

wherein $R_4$ is alkyl (e.g. $C_3-C_{12}$ alkyl), cycloalkyl (e.g. $C_3-C_{12}$ cycloalkyl) or aralkyl (e.g. $C_7-C_{15}$ aralkyl). The diacyl peroxides may include those as representable by the formula:

$$R_5-CO-O-O-CO-R_5 \quad (VI)$$

wherein $R_5$ is alkyl (e.g. $C_1-C_{20}$ alkyl), cycloalkyl (e.g. $C_3-C_{20}$ cycloalkyl), phenyl or halogen-substituted phenyl. As the peroxy esters, there are included those as represented by the formula:

$$R_6-CO-O-O-C(CH_3)_3 \quad (VII)$$

wherein $R_6$ is alkyl (e.g. $C_1-C_{12}$ alkyl), cycloalkyl (e.g. $C_3-C_{12}$ cycloalkyl), phenyl or substituted phenyl. Typical examples of the dialkyl peroxides include those represented by the formula:

$$R_7-O-O-R_7 \quad (VIII)$$

wherein $R_7$ is alkyl (e.g. $C_3-C_{12}$ alkyl), cycloalkyl (e.g. $C_3-C_{12}$ cycloalkyl) or aralkyl (e.g. $C_7-C_{15}$ aralkyl).

Specific examples of the organic peroxide are as follows: t-butyl hydroperoxide, cumene hydroperoxide, diisopropylbenzene hydroperoxide, p-menthane hydroperoxide, 2,5-dimethylhexane-2.5-dihydoperoxide, acetyl peroxide, propionyl peroxide, isobutyryl peroxide, octanoyl peroxide, decanoyl peroxide, stearoyl peroxide, benzoyl peroxide, p-chlorobenzoyl peroxide, 2,4-dichlorobenzoyl peroxide, diisopropyl peroxycarbonate, t-butyl peroxyacetate, t-butyl peroxyisobutyrate, t-butyl peroxypivalate, t-butyl peroxy-2-ethylhexanoate, t-butyl peroxylaurate, t-butyl peroxybenzoate, di-t-butyl peroxyphthalate, 2,5-dimethyl-2,5-di(benzoylperoxy)hexane, t-butyl peroxymaleate, t-butyl peroxyisopropylcarbonate, di-t-butyl peroxide, dicumyl peroxide, butylcumyl peroxide, etc. The amount of the organic peroxide is not limitative and usually may be from 1 to 200 % by mol (preferably from 10 to 50% by mol) based on the amount of olefin.

As for the reaction temperature, low temperatures are generally more favorable for the optical yield than are high temperatures. However, temperatures that are too low decrease the rate of reaction so that the reaction temperature is generally from about −30 to 150° C and preferably from about −10 to 100° C. The use of a solvent is not essential, but there may be employed ordinary organic solvents such as acetonitrile, propinitrile, pyridine, picoline, benzene, toluene, acetic acid and propionic acid. The amount of the solvent is not particularly limited, and in general an amount of one-tenth to one hundred times by weight based on the organic peroxide is sufficient. When the reaction solvent is a mixture of a carboxylic acid such as acetic acid and a solvent having a nitrogen atom capable of forming a coordinate bond such as acetonitrile or pyridine, the rate of reaction can be increased by using metallic copper as an additive. The concentration of the catalysts is not particularly limited, and the amount is generally from about 0.1 to 100% by mole, preferably from about 1 to 20% by mole, based on the organic peroxide.

After completion of the reaction, the catalyst may be recovered for reuse by any conventional separation procedure.

As the result of the reaction, there is produced the objective optically active allylic ester of which the ester part is originated from the corresponding moiety present in the reaction system. Such moiety may, for instance, come from the organic peroxide or the solvent. When the organic peroxide is the hydroperoxide (V) or the dialkyl peroxide (VIII) which does not have any acyl moiety, the ester part may be originated from any solvent having an acyl moiety such as acetic acid or propionic acid. When the organic peroxide is the diacyl peroxide (VI) or the peroxy ester (VII) which has an acyl moiety, the ester part may be originated from such acyl moiety and/or, if any solvent having an acyl moiety is used, from the acyl moiety in the solvent.

The optically active allylic esters obtained by the present invention have various uses. For example, methyl styryl carbinyl acetate is useful as a perfume. Further, for example, verbenyl acetate and pulegyl acetate are useful as intermediates in the synthesis of menthol. When the optically active allylic esters are subjected to hydrogenation and/or hydrolysis, there are produced optically active esters or optically active alcohols, which are also per se useful or intermediates in the synthesis of other per se useful substances as medicines, agricultural chemicals, perfumes and the like. For example, 3-octanol and 3-nonanol derived from the corresponding allylic esters obtained by the present invention are used as fruit essence and for compounding a rose perfume, respectively. Further, for example, 1-octen-3-ol is known as matsutake-ol and can be used as a flavoring agent for food. In addition, the optically active alcohols are useful as reagents for analyzing optically active carboxylic acids.

The present invention will be illustrated in detail with reference to the following examples, which are not however to be interpreted as limiting the invention thereto. It may be apparent that, when the catalysts used in these examples are replaced by the optical enantiomers thereof, the resulting esters are the corresponding enantiomers.

EXAMPLE 1

A mixture of 0.631 g of (S)-(—)-N-salicylidene-1-phenyl-2-(p-tolyl)ethylamine, 0.182 g of cupric acetate, 0.70 g of copper powder, 15 ml of acetonitrile, 10 ml of ethyl acetate, 5 ml of acetic acid, 15 ml of cyclohexene and 5 ml of t-butyl peroxybenzoate was stirred at 0° C for 24 hours in a nitrogen atmosphere. After removing the residual copper powder by filtration, the filtrate was admixed with 50 ml of benzene. The organic layer was successively washed with a 2N aqueous hydrochloric acid solution, water, an aqueous solution saturated with sodium hydrogen carbonate and an aqueous solution saturated with sodium chloride, and dried over anhydrous sodium sulfate. After evaporating the solvent, the residue was distilled under reduced pressure to obtain 1.90 g or 2-cyclohexenyl acetate. B.P. 75°–76° C/21 mmHg.

Optical rotation $\alpha_D$ —33.00° (neat, 1 dm)

The ester thus obtained was hydrolyzed with a 6% sodium hydroxide solution (water/methanol = 5/3 by weight) by the usual method to obtain 2-cyclohexenol.

Optical rotation $\alpha_D$ —21.36° (neat, 1 dm)

EXAMPLE 2

A mixture of 0.50 g of the copper complex of (S)-(—)-N-salicylidene-1-phenyl-2-(p-tolyl)ethylamine, 0.045 g of copper powder, 25 ml of cyclohexene, 25 ml of acetonitrile, 5 ml of acetic acid and 5 ml of t-butyl peroxybenzoate was heated with stirring at 70° C for 7 hours in a nitrogen atmosphere. After cooling, the reaction mixture was admixed with 50 ml of benzene, washed successively with a 2N aqueous hydrochloric acid solution, water, an aqueous solution saturated with sodium hydrogen carbonate and an aqueous solution saturated with sodium chloride, and dried over anhydrous sodium sulfate. After evaporating the solvent, the residue was distilled under reduced pressure to obtain 1.88 g of 2-cyclohexenyl acetate. B.P. 75°–76° C/21 mmHg.

Optical rotation $\alpha_D$ —7.75° (neat, 1 dm)

EXAMPLE 3

The reaction in Example 2 was carried out at room temperature for 6 days to obtain 1.38 g of 2-cyclohexenyl acetate.

Optical rotation $\alpha_D$ —16.80° (neat, 1 dm)

EXAMPLE 4

A mixture of 0.451 g of (S)-(+)-N-salicylidene-1-phenylethylamine, 0.182 g of cupric acetate, 0.7 g of copper powder, 15 ml of cyclohexene, 15 ml of acetonitrile, 5 ml of acetic acid and 5 ml of t-butyl peroxybenzoate was stirred at 20° to 25° C for 6.5 hours in a nitrogen atmosphere. After the reaction, the reaction mixture was treated in the same manner as in Example 1 to obtain 1.60 g of 2-cyclohexenyl acetate.

Optical rotation $\alpha_D$ —23.69° (neat, 1 dm)

The ester thus obtained was reduced with lithium aluminum hydride by the usual method to obtain 2-cyclohexenol.

Specific rotation $[\alpha]_D$ —12.41° (c 3.96, chloroform)

EXAMPLES 5 TO 8

In the same manner as in Example 1, the asymmetric oxidations fo cyclohexene were carried out under different conditions. The results are shown in Table 1.

Table 1

| Example No. | Catalyst system | (g) | Solvent | (ml) | Cyclohexene (ml) | t-Butyl peroxybenzoate (ml) | Reaction temperature (° C) | Reaction time (hr) | 2-Cyclohexenyl acetate $\beta_D$ (neat, 1 dm) | Yield (g) |
|---|---|---|---|---|---|---|---|---|---|---|
| 5 | PTE-Sal<br>Cu(OAc)$_2$<br>Cu° | 0.630<br>0.182<br>0.70 | CH$_3$CN<br>AcOH | 15<br>5 | 15 | 5 | 20–25 | 4 | —24.26° | 1.60 |
| 6 | PTE-Sal<br>Cu(OAc)$_2$<br>Cu° | 1.260<br>0.182<br>0.70 | CH$_3$CN<br>AcOH | 15<br>5 | 15 | 5 | 20–25 | 3 | —29.61° | 1.50 |
| 7 | PA-Sal<br>Cu(OAc)<br>Cu° | 0.451<br>0.123<br>0.50 | CH$_3$CN<br>C$_6$H$_6$<br>AcOH | 15<br>5<br>5 | 15 | 5 | 20–25 | 6 | —22.54° | 2.10 |
| 8 | PA-Sal<br>Cu(OAc)$_2$ | 0.902<br>0.364 | C$_6$H$_6$<br>AcOH | 60<br>3 | 15 | 5 | 75 | 12 | —4.66° | 2.90 |

Note) Explanation of the symbols in the table:
PTE-Sal: (S)-(—)-(N)-salicylidene-1-phenyl-2-(p-tolyl)ethylamine
PA-Sal: (S)-(+)-(N)-salicylidene-1-phenylethylamine
Cu(OAc)$_2$: Cupric acetate
Cu°: Copper powder
AcOH: Acetic acid

EXAMPLE 9

In Example 5, the t-butyl peroxybenzoate was replaced by 5 ml of t-butyl peroxyacetate (30% solution), whereby 0.60 g of 2-cyclohexenyl acetate was obtained.

Optical rotation $\alpha_D$ —31.83° (neat, 1 dm)

EXAMPLE 10

A mixture of 0.225 g of (S)-(+)-N-salicylidene-1-phenylethylamine, 0.009 g of cuprous chloride, 20 ml of cyclohexene, 10 ml of acetonitrile and 5 ml of t-butyl peroxybenzoate was heated with stirring at 70° C for 32 hours in a nitrogen atmosphere. Thereafter, the reaction mixture was treated in the same manner as in Example 1 to obtain 3.75 g of 2-cyclohexenyl benzoate.

Optical rotation $\alpha_D$ —3.20° (neat, 1 dm)

EXAMPLE 11

A mixture of 1.100 g of the copper complex of N-salicylidene-3-amino-3-deoxy-1,2-O-isopropylidene-5-O-triphenylmethyl-α-D-ribofuranose, 0.70 g of copper powder, 15 ml of acetonitrile, 5 ml of acetic acid, 15 ml of cyclohexene and 5 of t-butyl peroxybenzoate was stirred at room temperature for 9 hours in a nitrogen atmosphere. After filtering the reaction solution, the filtrate was treated in the same manner as in Example 1 to obtain 1.80 g of 2-cyclohexenyl acetate.

Optical rotation $\alpha_D$ −6.67° (neat, 1 dm)

EXAMPLE 12

In Example 4, the cyclohexene was replaced by 15 ml of cyclopentene to obtain 0.90 g of 2-cyclopentenyl acetate.

Optical rotation $\alpha_D$ −15.12° (neat 1dm)

EXAMPLE 13

In Example 12, 15 ml of 1-methylcyclohexene was used in place of the cyclopentene to obtain 1.70 g of a mixture of 2-methyl-2-cyclohexenyl acetate and 3-methyl-2-cyclohexenyl acetate.

Optical rotation $\alpha_D$ −1.69° (neat, 1 dm)

EXAMPLE 14

In Example 12, 15 ml of 1-hexene was used in place of the cyclopentene to obtain 0.35 g of hexenyl acetate.

Optical rotation $\alpha_D$ −0.35° (neat, 1 dm)

EXAMPLE 15

In Example 12, 15 ml of 1-octene was used in place of the cyclopentene to obtain 0.92 g of octenyl acetate.

Optical rotation $\alpha_D$ −0.05° (neat, 1 dm)

EXAMPLE 16

In Example 4, 1.328 g of (R)-(+)-N-salicylidene-2-amino-1,1-di-(o-octyloxy)-3-phenylpropanol-1 was used as the optically active Schiff's base to obtain 1.65 g of 2-cyclohexenyl acetate.

Optical rotation $\alpha_D$ +0.17° (neat, 1 dm)

EXAMPLE 17

A mixture of 0.6 g of di-L-prolinato Copper (II), 0.7 g of copper powder, 15 ml of acetonitrile, 5 ml of acetic acid, 15 ml of cyclohexene and 5 ml of t-butyl peroxybenzoate was stirred at 20° to 25° C for 3 hours in a nitrogen atmosphere. After it was confirmed on TLC (thin layer chromatography) that the residual t-butyl peroxybenzoate was no longer present, the remaining copper powder was filtered off and the filtrate was admixed with 50 ml of benzene. The organic layer was successively washed with a 2N hydrochloric acid, an aqueous solution saturated with sodium chloride, an aqueous solution saturated with sodium hydrogen carbonate and an aqueous solution saturated with sodium chloride, and dried over anhydrous sodium sulfate. After removing the solvent, the residue was distilled under reduced pressure to obtain 1.40 g of 2-cyclohexenyl acetate. B.P. 75°–76° C/21 mmHg.

Optical rotation $\alpha_D$ −47.40° (neat, 1 dm)

EXAMPLE 18

A mixture of 0.3 g of di-L-prolinato Copper (II), 15 ml of cyclohexene, 20 ml of acetic acid and 5 ml of t-butyl peroxybehzoate was heated with stirring at 90° C for 5 hours in a nitogen atmosphere. After cooling, the reaction mixture was treated in the same manner as in Example 1 to obtain 2.50 g of 2-cyclohexenyl acetate.

Optical rotation $\alpha_D$ −28.50° (neat, 1 dm)

EXAMPLES 19 TO 22

In the same manner as in Example 17, the asymmetric oxidations of cyclohexene were carried out under different conditions. The results are shown in Table 2.

Table 2

| Example No. | Catalyst system (g) | | t-Butyl peroxy-benzoate (ml) | 2-Cyclohexenyl acetate | |
|---|---|---|---|---|---|
| | | | | $\beta_D$ (neat, 1 dm) | Yield (g) |
| 19 | L-Alanine | 0.36 | 5 | −5.46° | 2.10 |
| | Cu(OAc)$_2$ | 0.182 | | | |
| | Cu° | 0.70 | | | |
| 20 | Di-D-Phenylalaninato Copper (II) | 0.50 | 5 | +11.16° | 2.15 |
| | Cu° | 0.50 | | | |
| 21 | N,N-Dimethyl-D-phenylalanine | 0.193 | 5 | −3.50° | 1.90 |
| | Cu(OAc)$_2$ | 0.091 | | | |
| | Cu° | 0.35 | | | |
| 22 | N-(2-Cyanoethyl)-D-phenylalanine | 0.437 | 5 | +13.39° | 2.00 |
| | Cu(OAc)$_2$ | 0.182 | | | |
| | Cu° | 0.70 | | | |

EXAMPLES 23 TO 44

In the same manner as in Example 18, the asymmetric oxidations of cyclohexene were carried out under different conditions. The results are shown in Table 3.

Table 3

| Example No. | Catalyst system (g) | | Solvent (ml) | Cyclohexene (ml) | t-Butyl peroxybenzoate (ml) | Reaction temperature (° C) | 2-Cyclohexenyl acetate | |
|---|---|---|---|---|---|---|---|---|
| | | | | | | | $\beta_D$ (Neat, 1 dm) | Yield (g) |
| 23 | Di-L-Prolinato Copper (II) | 0.30 | AcOH 20 | 15 | 5 | 80 | −38.19° | 2.40 |
| 24 | Di-L-Prolinato Copper (II) | 0.30 | AcOH 20 | 15 | 5 | 95 | −28.50° | 2.50 |
| 25 | Di-D-Phenylalaninato Copper (II) | 0.45 | AcOH 40 CH$_3$CN 20 | 15 | 5 | 70 | +20.96° | 1.40 |
| 26 | Bis-N,N-Dimethyl-D-phenylanalinato Copper (II) | 0.30 | AcOH 20 | 15 | 5 | 70 | −2.15° | 2.70 |
| 27 | Di-L-Oxyprolinato Copper (II) | 0.265 | AcOH 50 | 15 | 5 | 70 | −45.50° | 2.25 |

Table 3-continued

| Example No. | Catalyst system (g) | | Solvent (ml) | Cyclohexene (ml) | t-Butyl peroxybenzoate (ml) | Reaction temperature (° C) | 2-Cyclohexenyl acetate | |
|---|---|---|---|---|---|---|---|---|
| | | | | | | | $\beta_D$ (Neat, 1 dm) | Yield (g) |
| 28 | Bis-D-(p-Methylsulfonylphenyl) serinato Copper (II) | 0.583 | AcOH 50 | 15 | 5 | 70 | +3.02° | 2.75 |
| 29 | L-Alanine | 0.180 | AcOH 20 | 15 | 5 | 80 | −7.34° | 2.80 |
| | Cu(OAc)$_2$ | 0.182 | | | | | | |
| 30 | L-Leucine | 0.262 | AcOH 50 | 10 | 5 | 70 | −14.40° | 2.30 |
| | Cu(OAc) | 0.182 | | | | | | |
| 31 | D-Phenylalanine | 0.336 | AcOH 40 | 10 | 5 | 70 | +20.86° | 2.15 |
| | Cu(OAc)$_2$ | 0.182 | | | | | | |
| 32 | L-Proline | 2.30 | AcOH 50 | 20 | 15 | 70 | −21.43° | 6.60 |
| | Cu(OAc)$_2$ | 0.182 | | | | | | |
| 33 | D-Phenylglycine | 0.302 | AcOH 50 | 15 | 5 | 70 | +1.54° | 2.30 |
| | Cu(OAc)$_2$ | 0.182 | | | | | | |
| 34 | L-Valine | 0.234 | AcOH 40 | 10 | 5 | 70 | −21.55° | 2.20 |
| | Cu(OAc) | 0.182 | | | | | | |
| 35 | N-(n-Butyl)-L-alanine | 0.290 | AcOH 20 | 15 | 5 | 70 | +2.70° | 2.65 |
| | Cu(OAc)$_2$ | 0.182 | | | | | | |
| 36 | N-Methyl-L-proline | 0.230 | AcOH 30 | 15 | 5 | 70 | +7.60° | 2.60 |
| | Cu(OAc)$_2$ | 0.182 | | | | | | |
| 37 | N-Benzyl-D-phenylalanine | 0.511 | AcOH 30 | 15 | 5 | 70 | −26.60° | 2.40 |
| | Cu(OAc)$_2$ | 0.182 | | | | | | |
| 38 | N-Benzyl-D-phenylglycine | 0.483 | AcOH 30 | 10 | 5 | 70 | −2.28° | 2.35 |
| | Cu(OAc)$_2$ | 0.182 | | | | | | |
| 39 | N-Benzyl-L-valine | 0.414 | AcOH 30 | 10 | 5 | 70 | +12.35° | 2.30 |
| | Cu(OAc)$_2$ | 0.182 | | | | | | |
| 40 | N-(2-Cyanoethyl)-L-leucine | 0.368 | AcOH 30 | 15 | 5 | 70 | +3.26° | 2.60 |
| | Cu(OAc)$_2$ | 0.182 | | | | | | |
| 41 | N-(2-Cyanoethyl)-L-alanine | 0.248 | AcOH 30 | 20 | 5 | 70 | −2.65° | 2.40 |
| | Cu(OAc)$_2$ | 0.182 | | | | | | |
| 42 | L-Proline | 0.690 | AcOH 50 | 20 | 15 | 70 | −44.20° | 6.90*1 |
| | Cu(OAc)$_2$ | 0.182 | | | | | | |
| 43 | L-Proline | 0.077 | CH$_3$CN 20 | 20 | 5 | 70 | | *2 |
| | Cu(OAc)$_2$ | 0.182 | C$_6$H$_6$ 20 | | | | | |
| 44 | L-Valine | 0.234 | AcOH 40 | 15 | 15 | 70 | −13.57° | 6.47*3 |
| | Cu(OAc)$_2$ | 0.182 | | | | | | |

Note) *1: 1.07 g of 2-cyclohexenyl benzoate was obtained in addition to 2-cyclohexenyl acetate. The optical rotation of the benzoate ($\alpha_D$) was −45.72° (neat, 1 dm).
*2: The product was 4.15 g of 2-cyclohexenyl benzoate. Its optical rotation ($\alpha_D$) was −21.12° (neat, 1 dm).
*3: 1.45 g of 2-cyclohexenyl benzoate was obtained in addition to 2-cyclohexenyl acetate. The optical rotation of the benzoate ($\alpha_D$) was −14.13° (neat, 1 dm).

EXAMPLES 45 AND 46

In the same manner as in Example 18, the asymmetric oxidations of 1-octene and cyclopentene were carried out. The results are shown in Table 4.

Table 4

| Example No. | Catalyst system (g) | Solvent (ml) | Olefin (ml) | t-Butyl peroxybenzoate (ml) | Reaction temperature (° C) | Product | | Yield (g) |
|---|---|---|---|---|---|---|---|---|
| | | | | | | Acetate | $\alpha_D$ (neat, 1 dm) | |
| 45 | L-Proline 0.230 Cu(OAc)$_2$ 0.182 | AcOH 20 | 1-octene 10 | 5 | 70 | Octenyl | +0.07° | 1.05 |
| 46 | L-Proline 0.230 Cu(OAc)$_2$ 0.182 | AcOH 20 | 1-Cyclopentene 10 | 5 | 70 | 2-Cyclopentenyl acetate | −7.39° | 1.42 |

EXAMPLE 47

The reaction was carried out in the same manner as in Example 11 except that the copper complex was replaced by 0.582 g of the cupric complex of the Schiff's base of the formula (I) wherein X and Y are each a hydrogen atom and R$_0$ is a menthyl group having the same absolute configuration as that of l-menthol. As the result, 1.95 g of 2-cyclohexenyl acetate was obtained.

Optical rotation $\alpha_D$ −7.20° (neat, 1 dm)

EXAMPLE 48

The reaction was carried out in the same manner as in Example 4 except that the Schiff's base was replaced by 0.780 g of the Schiff's base obtained from dehydroabiethylamine and salicylaldehyde. As the result, 2.00 g of 2-cyclohexenyl acetate was obtained.

Optical rotation $\alpha_D$ −2.48° (neat, 1 dm)

What is claimed is:

1. In the preparation of olefin derivatives having an ester group at the allylic position which comprises reacting an olefin having at least one hydrogen atom at the allylic position and which will produce an allylic ester having an asymmetric carbon atom with an organic peroxide in the presence of a copper catalyst, a method for producing optically active allylic esters which comprises using, as the copper catalyst, a catalytic amount of an optically active copper complex prepared by the treatment of a copper compound with an optically active Schiff's base of the formula:

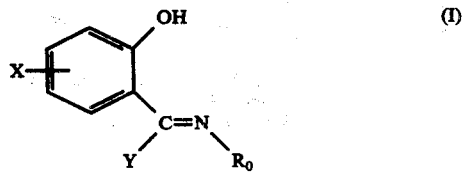

or an optically active amino acid of the formula:

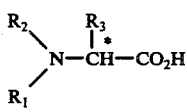
(II)

wherein $R_0$ is an optically active moiety selected from the group consisting of $C_4$–$C_{20}$ alkyl, $C_4$–$C_{20}$ cycloalkyl and $C_8$–$C_{20}$ aralkyl which may contain an unsaturated bond and/or a $C_1$–$C_{20}$ alkoxy group, hydroxy, chlorine or bromine; X and Y are each hydrogen, halogen, $C_1$–$C_4$ alkyl, $C_5$–$C_8$ cycloalkyl, $C_7$–$C_{15}$ aralkyl, $C_6$–$C_{12}$ aryl or $C_1$–$C_4$ alkoxy, $R_1$ and $R_2$ are each $C_1$–$C_{10}$ alkyl, $C_7$–$C_{15}$ aralkyl or $C_6$–$C_{15}$ aryl which may contain an unsaturated bond and/or halogen, a $C_1$–$C_{10}$ alkoxy group, cyano or amino, $R_3$ is $C_1$–$C_{10}$ alkyl, cyclohexyl, $C_7$–$C_{10}$ aralkyl or $C_6$–$C_{10}$ aryl which may contain an unsaturated bond and/or halogen, a $C_1$–$C_{10}$ alkoxy group, hydroxyl or methylsulfonyl, or when $R_3$ is linked together with $R_2$, they form trimethylene or tetramethylene optionally substituted with halogen, hydroxyl or a $C_1$–$C_{10}$ alkoxy group, and the asterisk (*) indicates an asymmetric carbon atom, the ester moiety in said allylic ester being derived from the organic peroxide and/or the solvent in which the reaction is conducted if a solvent is used, at least one of said organic peroxide and said solvent having an acyl moiety from which to form said ester moiety.

2. The method according to claim 1, wherein the olefin is selected from the group consisting of $C_4$–$C_{12}$ acyclic olefins, $C_5$–$C_{12}$ cyclic olefins, $C_9$–$C_{24}$ aromatic group-substituted olefins and derivatives thereof substituted with chlorine, bromine, alkyl groups having not more than 4 carbon atoms, alkoxy groups having not more than 4 carbon atoms, alkanoyl or alkoxycarbonyl groups having not more than 10 carbon atoms or alkanoyloxy groups having not more than 10 carbon atoms.

3. The method according to claim 1, wherein the olefin is selected from the group consisting of $C_4$–$C_{12}$ acyclic olefins, $C_5$–$C_{12}$ cyclic olefins, $C_9$–$C_{24}$ aromatic group-substituted olefins and derivatives thereof substituted with halogen, alkyl, alkoxy, alkanoyl, alkoxycarbonyl or alkanoyloxy.

4. The method according to claim 1, wherein the organic peroxide is selected from the group consisting of hydroperoxides, diacyl peroxides, peroxy esters and dialkyl peroxides.

5. The method according to claim 1, wherein the reaction is carried out at a temperature of from about −30° to 150° C.

6. The method according to claim 1, wherein the reaction is carried out in the absence of a solvent.

7. The method according to claim 1, wherein the reaction is carried out in the presence of a solvent.

8. The method according to claim 7, wherein the solvent is acetonitrile, propionitrile, pyridine, picoline, benzene, toluene, acetic acid or propionic acid.

9. The method according to claim 7, wherein the reaction is carried out in the presence of metallic copper.